(12) United States Patent
Lange et al.

(10) Patent No.: US 9,072,550 B2
(45) Date of Patent: Jul. 7, 2015

(54) SPINAL FIXATION SYSTEM AND METHOD (71) Applicant: Warsaw Orthopedic, Inc., Warsaw, IN (US)

(72) Inventors: Eric C. Lange, Collierville, TN (US); Darren L. Davis, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 132 days.

(21) Appl. No.: 13/839,568

(22) Filed: Mar. 15, 2013

(65) Prior Publication Data
US 2014/0277171 A1 Sep. 18, 2014

(51) Int. Cl.
*A61B 17/70* (2006.01)
(52) U.S. Cl.
CPC .................................. *A61B 17/7068* (2013.01)
(58) Field of Classification Search
CPC ........... A61B 17/7062; A61B 17/7067; A61B 17/7068

USPC ........................ 606/246, 248, 249, 60, 279; 623/17.11–17.16
See application file for complete search history.

(56) References Cited

U.S. PATENT DOCUMENTS

| | | | |
|---|---|---|---|
| 7,048,736 B2 | 5/2006 | Robinson et al. | |
| 7,727,233 B2 | 6/2010 | Blackwell et al. | |
| 7,803,190 B2 | 9/2010 | Zucherman et al. | |
| 8,206,420 B2 | 6/2012 | Patel et al. | |
| 8,241,330 B2 | 8/2012 | Lamborne et al. | |
| 2002/0143331 A1 | 10/2002 | Zucherman et al. | |
| 2008/0183211 A1* | 7/2008 | Lamborne et al. | 606/249 |
| 2010/0211101 A1 | 8/2010 | Blackwell et al. | |
| 2012/0253393 A1 | 10/2012 | Fiorella | |

* cited by examiner

*Primary Examiner* — Ellen C Hammond
*Assistant Examiner* — Christina Negrellirodrigue (57) ABSTRACT

A spinal fixation system includes a first plate, a post fixedly attached to the first plate and extending transverse therefrom. A second plate receives the distal end of the post. A locking mechanism is configured to restrict at least one of axial translation and/or orbital rotation of the second plate with respect to the post. The locking mechanism can include a locking nut having two non-concentric cylinders which enable an interference fit between the nut and the post, thus restricting axial translation of the second plate.

19 Claims, 7 Drawing Sheets

SPINAL FIXATION SYSTEM AND METHOD

TECHNICAL FIELD

The present disclosure generally relates to medical devices for the treatment of musculoskeletal disorders surgery, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as fixation devices, for stabilization of a treated section of a spine. This disclosure describes an improvement over these prior art technologies.

SUMMARY

Accordingly, a surgical system and method for correction of a spine disorder is provided. In one embodiment, in accordance with the principles of the present disclosure, the spinal fixation system includes a first plate configured to be positioned between spinal processes of two adjacent vertebrae, and a post having one end fixedly attached to the first plate and a distal second end. A second plate is positioned opposite said first plate and configured to receive the distal end of the post. The second plate can be axially translated along the post to a desired position.

According to another embodiment, in accordance with the principles of the present disclosure, the spinal fixation system includes a first plate configured to be positioned on one side of two spinal processes of two adjacent vertebrae, and a post having one end fixedly attached to the first plate and a distal second end. A second plate is positioned on an opposite side of the two spinal processes and is configured to receive the distal end of the post. The second plate being capable of at least axial translation along the post. A locking mechanism cooperative with the post and the second plate locks and restricts at least one of axial translation and orbital rotation of the second plate with respect to the post.

In one embodiment, a method for correction of a spine disorder is provided. The method comprises the steps of: providing access to a surgical site at a selected section of a spine; providing a spinal fixation system including a first plate configured to be positioned on one side of two spinal processes of two adjacent vertebrae and a post having one end fixedly attached to the first plate and a distal second end. A second plate is positioned on an opposite side of the two spinal processes and is configured to receive the distal end of the post. The second plate being capable of at least axial translation along the post. A locking mechanism cooperates with the post and the second plate to lock and restrict at least one of axial translation and orbital rotation of the second plate with respect to the post. The method further including positioning the first plate against the two spinal processes; positioning the second plate onto the post; adjusting an axial position of the second plate along the post; adjusting an orbital rotation position of the second plate with respect to said post; and locking the axial translation and orbital rotation position using the locking mechanism.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the surgical system and related methods of use disclosed are discussed in terms of medical devices for the treatment of musculoskeletal disorders and more particularly, in terms of a surgical system and method for correction of a spine disorder. It is envisioned that the surgical system and method may be employed in applications such as correction of deformities such as kyphosis, scoliosis. For example, the surgical system and method can include an Interspinous process plate fixation device.

According to one aspect, this disclosure involves an Interspinous process plate fixation device configured for surgical implantation at a bone site. In some embodiments, the fixation device is provided which is specifically designed to fuse two adjacent interspinous processes and/or lamina. For example, one embodiment involves two plates positioned on opposing sides of spinal processes and a post adjustably connecting/securing the two plates to each other. A locking nut configured to be received by the post can allow for both orbital motion and translation of the fixation device.

It is contemplated that one or all of the components of the surgical system may be disposable, peel-pack, pre-packed sterile devices. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of Interspinous process plate fixation device 10 can be fabricated from biologically acceptable materials suitable for medical applications, including metals, synthetic polymers, ceramics and bone material and/or their composites, depending on the particular application and/or preference of a medical practitioner. For example, the components of Interspinous process plate fixation device 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of correction system 10 may have material composites, including the above materials, to achieve various desired characteristics such as strength, rigidity, elasticity, compliance, biomechanical performance, durability and radiolucency or imaging preference. The components of Interspinous process plate fixation device 10, individually or collectively, may also be fabricated from a heterogeneous material such as a combination of two or more of the above-described materials. The components of Interspinous process plate fixation device 10 may be monolithically formed, integrally connected or include fastening elements and/or instruments, as described herein.

Interspinous process plate fixation device 10 is employed, for example, with an open, mini-open or minimally invasive surgical technique to provide stabilization of a spine or other musculoskeletal structure. In preferred embodiments, the Interspinous process plate fixation device 10 is configured to be integrated with instrumentation to allow for one hand insertion and implantation to stabilize two adjacent vertebrae for any surgical procedure requiring the same.

In one embodiment, the system includes a first plate configured to be positioned between spinal processes of two adjacent vertebrae and a post having one end fixedly attached to the first plate and a distal second end. The system also includes a second plate positioned opposite the first plate and configured to receive the distal end of the post in a configuration that the second plate is capable of at least axial translation along the post.

In another embodiment a method for correction of a spine disorder, using the system of the disclosure is provided. The method comprises the steps of: providing access to a surgical site at a selected section of a spine; providing a spinal fixation system according to the disclosure including a first plate configured to be positioned on one side of two spinal processes of two adjacent vertebrae and a post having one end fixedly attached to the first plate and a distal second end. The system also includes a second plate positioned on an opposite side of the two spinal processes and being configured to receive the distal end of the post. The second plate is configured so as to at least axially translate along the post. A locking mechanism cooperative with the post and the second plate is provided to lock and restrict at least one of axial translation and orbital rotation of the second plate with respect to the post.

The method also includes positioning the first plate against the two spinal processes and positioning the second plate onto the post. Once in position, adjusting an axial position of the second plate along the post and adjusting an orbital rotation position of the second plate with respect to said post so as to arrive at the proper placement. Once properly placed, the axial translation and orbital rotation position is locked using the locking mechanism. The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures.

Turning now to FIGS. 1-10, there is illustrated components of a surgical system, such as, for example, an interspinous process plate fixation device 10 in accordance with the principles of the present disclosure.

Figure 1:
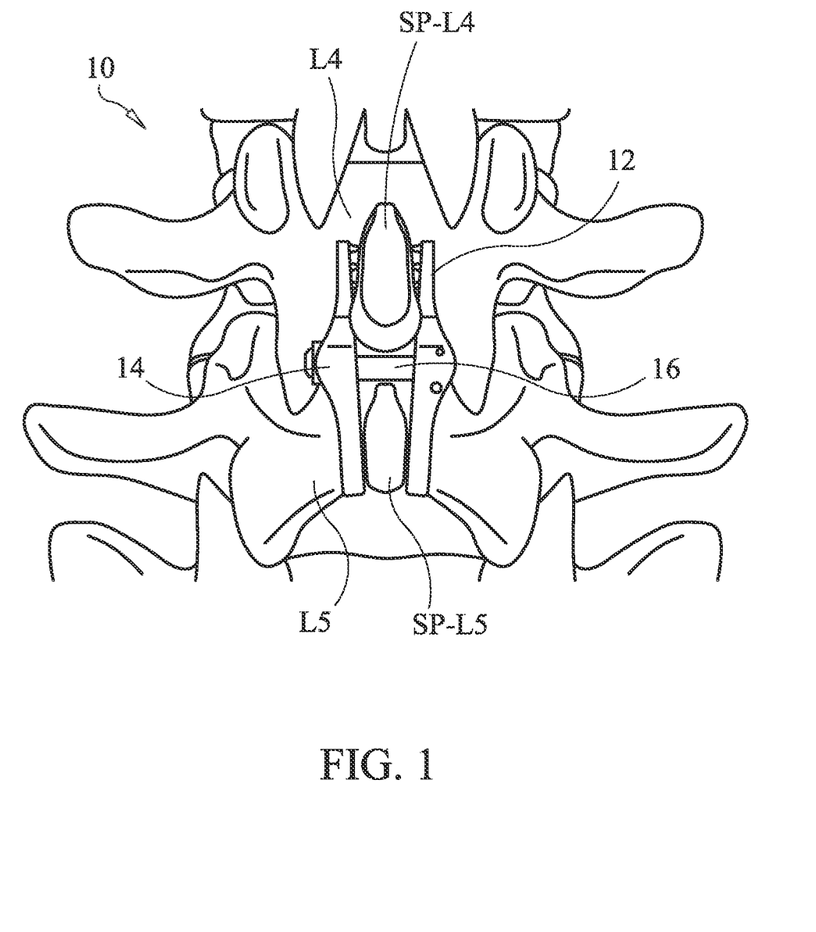
FIG. 1 is a posterior view of one embodiment of the components of the Interspinous process plate fixation device according to the principles of the present disclosure.

Referring to FIG. 1, Interspinous process plate fixation device 10 includes a first or head plate 12 configured to provide fixation with vertebrae along an axial or longitudinal direction of the spine. A second or locking plate 14 is provided that is connected to the plate 12 by a post 16. Second plate 14 is also configured to provide fixation with vertebrae along an axial or longitudinal direction of the spine. In the example of FIG. 1, the plates 12 and 14 of the fixation device 10 are shown attached to processes SP-L4 and SP-L5 of vertebrae L4 and L5, respectively, however it is understood that the present principles are not limited to this level of fixation only and is contemplated to provide restricted motion to all motion segments of the spine where applicable.

The plates 12 and 14 may include various cross sections, such as, e.g., oval, polygonal, U-shaped, irregular, uniform, non-uniform, variable, tapered, etc. as needed or desired. It is further envisioned that plate 12 and plate 14 may include a uniform thickness/diameter or may have various other configurations. In addition, the plate 12 and plate 14 may have various surface finishes, such as, for example, rough, threaded for connection with surgical instruments, arcuate, undulating, porous, semi-porous, dimpled, polished and/or textured according to the requirements of a particular application. It is contemplated that the shapes of the plates (12, 14) may be uniformly increasing or decreasing, or have alternate cross-section dimensions along their length. Further, plate 12 and plate 14 may have pre-defined curvatures (bends) along their length in furtherance of a surgical goal for a particular application.

The post 16 may include various cross sections, such as cylindrical, square, triangular, hexagonal, or any other geometrical cross sectional for which the plates and locking mechanisms are configured.

Figure 2:
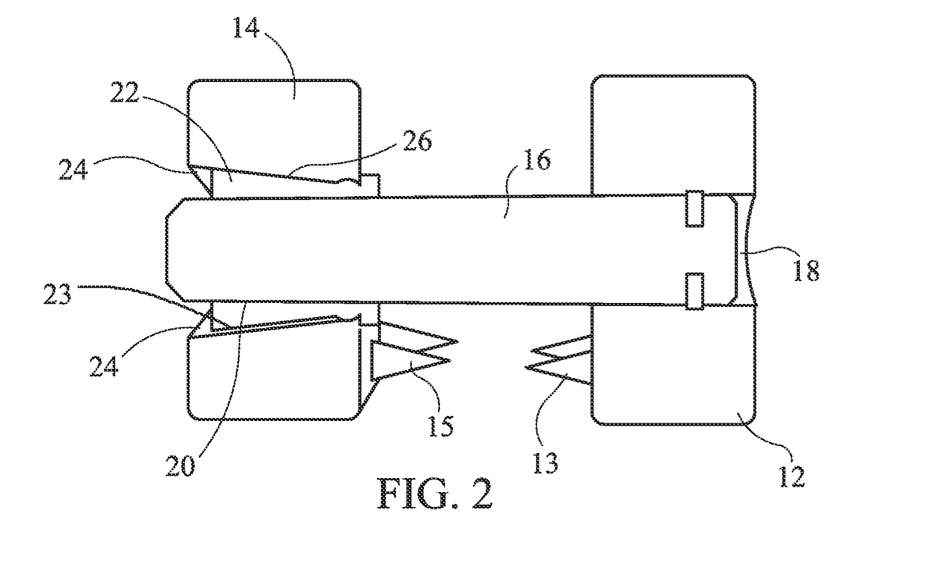
FIG. 2 is a cross sectional view of one embodiment of the Interspinous process plate fixation device shown FIG. 1 according to the principles of the present disclosure.

Referring to FIGS. 1 and 2, plate 12 is connected to post 16 by a connection mechanism 18. Connection mechanism 18 extends from the inboard face of plate 12 and does not allow for orbital rotation or translation once plate 12 and post 16 are adjoined together. Examples of connection mechanisms 18 for fixedly connecting plate 12 to post 16 can be, for example, via retaining ring, setscrew, pin, clamp or welding. The plate 16 provides for translation 20 along the axis of post 16. By way of example, the means for translation 20 can include a tapered collet 22 around post 16 and having an angular or tapered surface 23 that cooperates with a correspondingly angled or tapered inside or inboard surface 24 of plate 14, and through the axial movement of collet 22 toward plate 12, functions to lock the axial translation of plate 14 with respect to post 16. Plate 12 and 14 will often include spikes 13 and 15, respectively for engaging the spinal processes when the plates are locked into their operable fixation position.

The details of the locking mean 26 of the translation is explained in greater detail below with respect to FIGS. 5-10. The range of angles for the angular or tapered surface 23 of the means for translation 22 and the corresponding angular surface 24 of plate 14, could be, for example within the range of 1°-45° with respect to the central axis of post 16.

Figure 3:
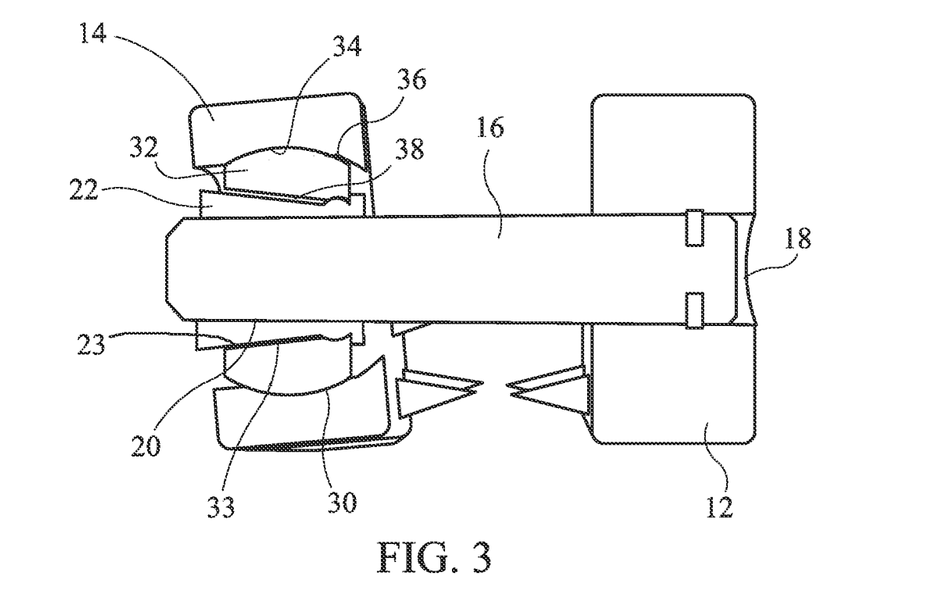
FIG. 3 is a cross sectional view of another embodiment of the Interspinous process plate fixation device shown FIG. 1 according to the principles of the present disclosure.

Referring to FIG. 3, there is shown a cross section of another embodiment of the Interspinous process plate fixation device. In this embodiment, plate 12 is fixedly connected 18 to post 16 that extends from the inboard face of plate 12 and does not allow for orbital rotation or translation once plate 12 and post 16 are adjoined together. Examples of means for connecting plate 12 to post 16 can be, for example, via retaining ring, setscrew, pin, clamp or welding. The plate 14 provides for translation 20 along the axis of post 16 and orbital rotation 30 about a point on the axis of the post. By way of example, the means for translation 20 can include a tapered collet 22 around post 16 and having an angular or tapered surface 23 that cooperates with a correspondingly angled inside surface 33 of a spherical collar 32, and through the axial movement of collet 22 toward plate 12, functions to lock the axial translation of plate 14, via spherical collar 32, with respect to post 16. The range of angles for the angular or tapered surface 26 of the means for translation 22 and the corresponding angular surface 24 of plate 14, could be, for example within the range of 1°-45° with respect to the central axis of post 16.

The means for orbital rotation 30 includes a spherical collar 32 having a convex outer surface 34 that cooperates with a concave inner surface 36 of plate 14, and an inner tapered or angular surface 33 that, as described above, cooperates with the tapered collet 22. The locking mechanism 38 included with plate 14 is described in more detail below with respect to FIGS. 5-10 below, and operates to lock the translation and/or orbital motion when plate 14 has been positioned and oriented as desired for the particular fixation application.

Figure 4:
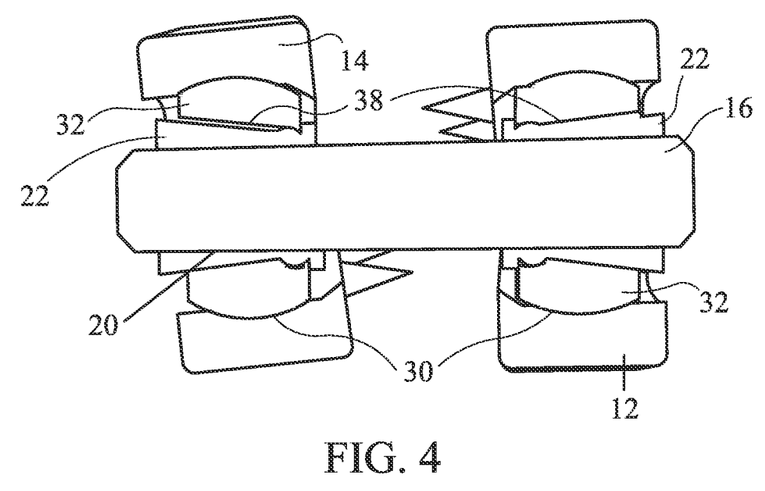
FIG. 4 is a cross sectional view of yet another embodiment of the Interspinous process plate fixation device shown FIG. 1 according to the principles of the present disclosure.

FIG. 4 shows another embodiment of the Interspinous process plate fixation device. In this implementation, both plates 12 and 14 are provide for translation 20 along the axis of post 16 and orbital rotation 30 about a point on the axis of the post 16. Both plates 12 and 14 contain the locking mechanism 38 to restrict translation and orbital rotation, or translation only.

Figure 5A:
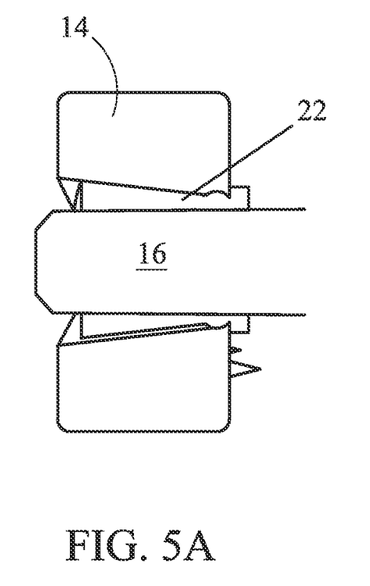
FIG. 5A is a cross-sectional view of a further embodiment of the Interspinous process plate fixation device showing a locking feature according to the principles of the present disclosure.
Figure 5B:
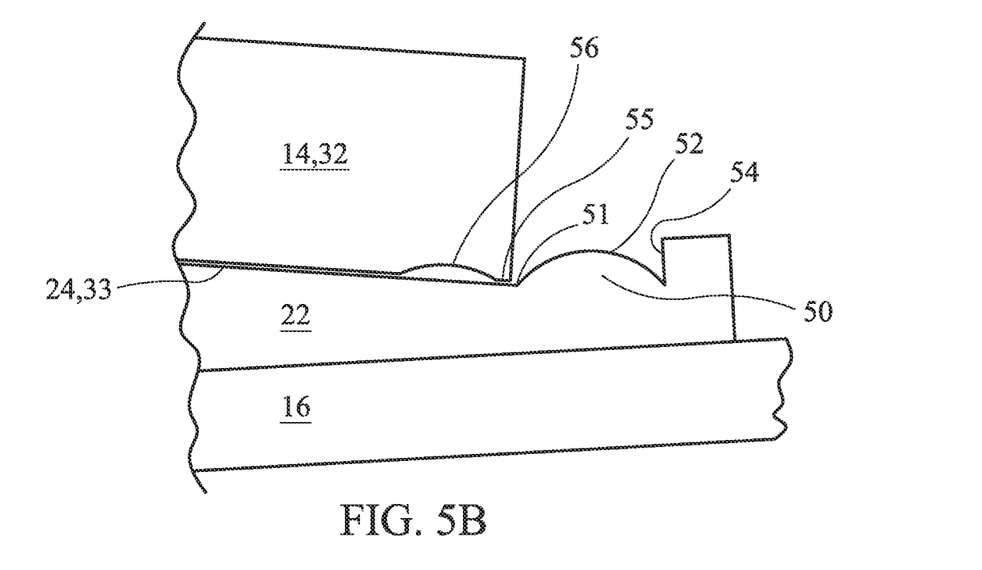
FIG. 5B is an enlarged cross sectional view of the locking feature shown in FIG. 5A in an unlocked position.
Figure 5C:
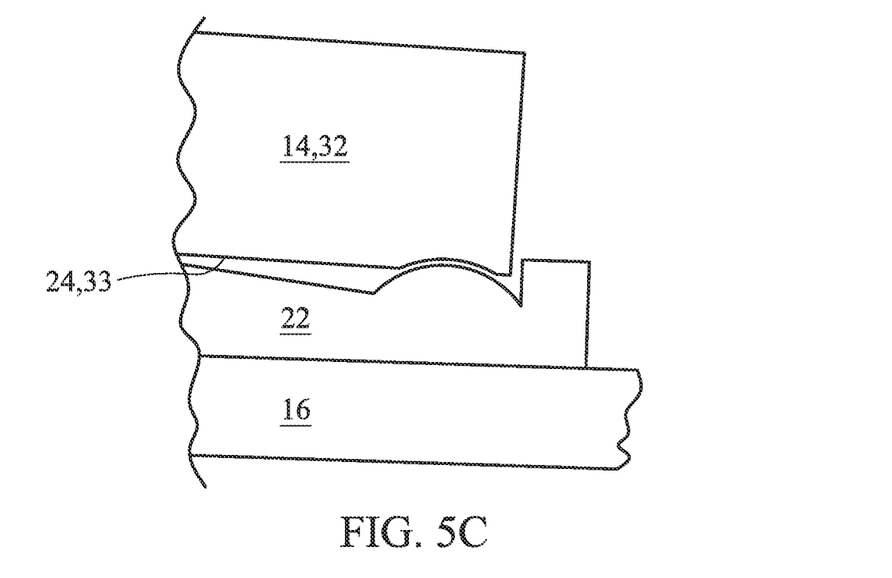
FIG. 5C is an enlarged cross sectional view of the locking feature shown in FIG. 5A in a locked position.

FIGS. 5A-5C show an implementation of the orbital and translational locking mechanism 26, 28 for the Interspinous process plate fixation device according to embodiments of the present principles. In one example, the tapered lock can be pressed into position so as to create an interference fit between the inside or inboard tapered surface 24 of plate 14 and the tapered collet 22. The applied force to engage the taper can occur by an instrument or the plate and collet can possess threads where a nut can create the applied force to lock the device. As collet 22 is slid in between plate 14 and post 16, it wedges plate 14 and post 16 together to lock plate 14 and post 16 in place. In one embodiment, as shown in FIG. 5C, tapered collet 22 includes a snap 50 feature which operates to prevent plate 14 and post 16 from sliding around as tapered collet 22 is inserted.

Figure 6:
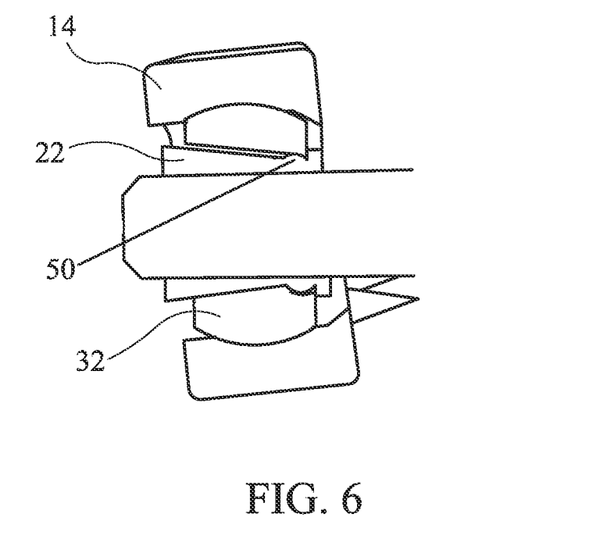
FIG. 6 is a cross-sectional view of yet a further embodiment of the Interspinous process plate fixation device showing an alternative locking feature according to the principles of the present disclosure.
Figures 7A, 7B:
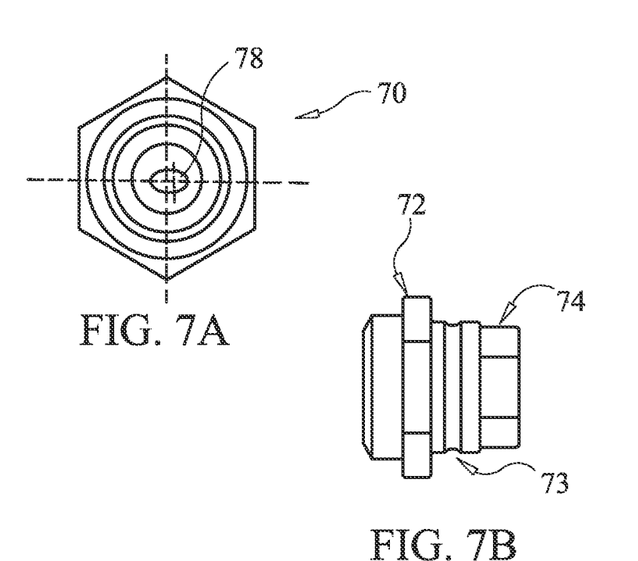
FIG. 7A is an end view of an embodiment of a locking nut used with the locking feature of the Interspinous process plate fixation device according to the principles of the present disclosure.
FIG. 7B is a side view of the locking nut shown in FIG. 7A.
Figure 7C:
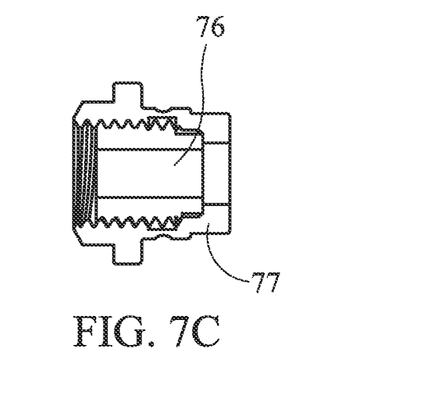
FIG. 7C is a side, cross sectional view of the locking nut shown in FIG. 7A.

As shown in FIGS. 5B, 5C and 6 snap 50 prevents plate 14 and post 16 from sliding around as collet 22 is inserted. Spherical collar 32 is pressed into position so as to create the interference fit between the inside taper 33 of the spherical collar and the tapered collet 22. The tapered collet 22 causes a frictional engagement of plate 14 and post 16. The applied force to engage the taper can occur by instrument or the spherical collar 32 and tapered collet 22 can possess threads where a nut can create the applied force to lock the fixation device. This locking feature 38 can restrict both translation and orbital motion of the plate 14. The spherical collar 32 includes a notch or slit 56 and as the tapered collet 22 is pressed further into the plate (toward the spinal process) against the sphere's inside taper 33, the locking feature will expand and cause the interference fit between the outside of the spherical collar 32 and the inside or inboard surface of plate 14. In an alternative configuration, the notch or slit 56 can be removed from the inner surface of spherical collar 32, thus retaining the orbital motion capability after translational motion has been restricted.

Referring to FIGS. 7A-7C and 8, there is shown a locking nut 70 according to another embodiment of the present principles. The locking nut 70 has two cylinders, an inner cylinder 76 and an outer cylinder 77, and preferably has an off center axis 78 between the two cylinders, such that the two cylinders are non-concentric. The locking nut 70 is configured such that the inner 76 and outer 77 cylinders can be threaded to a position which will align their inside hole features (i.e., central axes) and allow the receiving of the post 16. Upon rotation of one cylinder with respect to the other via distal nut 74, the non-concentric design of the cylinders will create an interference fit between both cylinders and the post. The outside cylinder 77 may or may not include a break off feature 73 to control applied torque (via distal nut 74) to lock the device onto the post. An outside cylinder removal nut 72 can be used for disengagement of the locking nut 70. This locking nut 70 feature can be used to restrict translation of the plate along the post 16. The inner threaded shaft of inner cylinder 76 is preferably keyed to the center post 16 so as to allow translation movement (before locking), but does not allow any rotation or orbital motion.

A spherical tip 80 on the outer cylinder not only provides an articulating surface between the tip and a correspondingly shaped surface 84 on the outboard surface of plate 14, but also functions to allow the plate 14 to orbit about a fixed point on the axis of the post 16. As will be evident from the drawing, the two non-concentric holes 82 of the inner cylinder 76 and the outer cylinder 77, as twisted, will lock onto the shaft/post 16, thus restricting any translational motion of the plate 14 with respect to the post 16.

In an alternative configuration, the inside cylinder 76 may be affixed to the outboard surface of plate 14 and the outside cylinder 77 of nut 72 is threaded away from the plate to lock the device. In this embodiment, locking of the locking nut 70 would restrict both orbital motion and translational motion of the plate.

Figure 8:
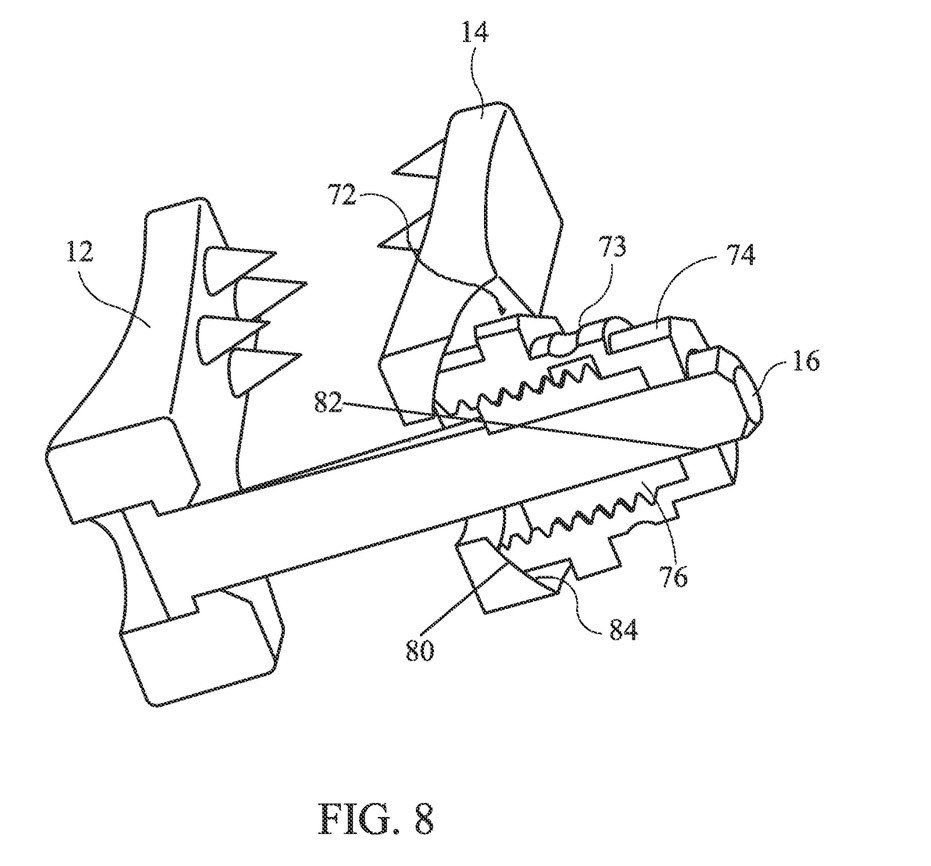
FIG. 8 is a cross-sectional view of an embodiment of the locking feature of the Interspinous process plate fixation device showing use of the locking nut of FIGS. 7A-7C.
Figure 9:
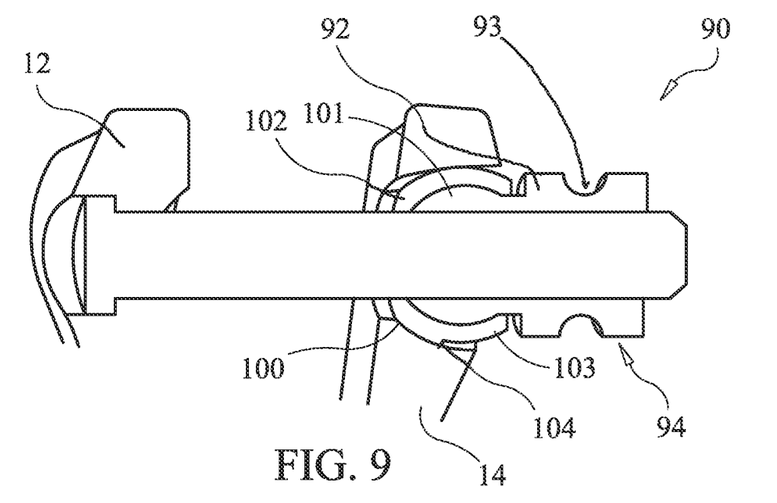
FIG. 9 is a perspective, cross-sectional view of a further embodiment of the Interspinous process plate fixation device showing another alternative locking feature according to the principles of the present disclosure.
Figure 10:
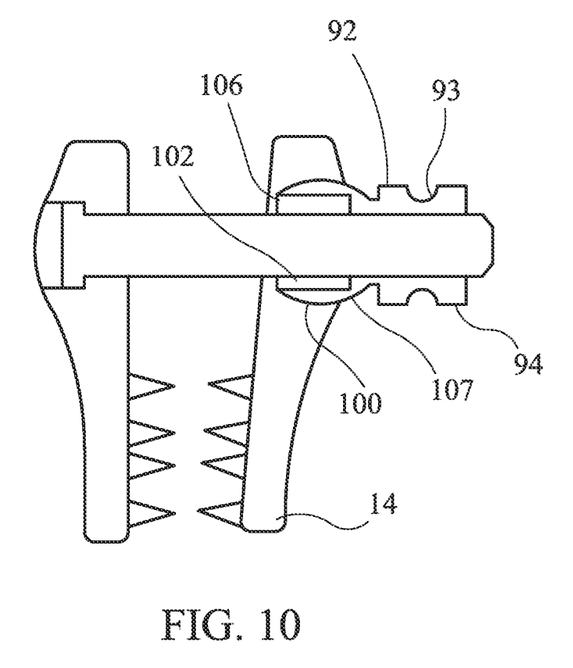
FIG. 10 is a side, cross-sectional view of the Interspinous process plate fixation device shown in FIG. 9.

FIGS. 9 and 10 show two different embodiments of a two-piece non-concentric/off center axes locking nut according to the present principles. Referring to FIG. 8 there is shown a locking nut 90 which can be twisted to a position that will align the two inside hole features of the two respective components (spherical end 101 and outer spherical feature 103) to allow insertion and smooth translation of plate 14 with respect to post 16. Nut 90 has a spherical end 101 which engages with an outer spherical feature 103. As with the embodiment of FIGS. 7-9, the holes in spherical end 101 and feature 103 are non-concentric 102, thus when operating in combination, the twisting of the distal hex nut 94 will rotate the two axes of the respective parts out of alignment to create an interference fit between the two piece locking nut 90 which will expand the locking nut and grip the inside of the plate 14 and post 16. The locking nut 90 may or may not include a break off feature 93 to control applied torque to lock the device onto the post. The proximal hex nut 92 can be used for disengagement of the locking nut. The articulating surface 100 of the tip of the outer spherical feature 107 of nut 90, and corresponding inside surface of the plate 14, in combination of with the twisting action of the two non-concentric holes (designated at 102) of the respective cylinders can restrict the translation of the plate along the post 16. According to one alternative configuration, the outer spherical feature 103 in this configuration can be slit 104 to allow expansion and interference within the plate 14 to lock both orbital and translational motion.

Alternatively, as shown in FIG. 10, the outer sphere 107 is not split and is integrated with nut 92 such that when twisting the outer cylinder via proximal hex nut 92, the non-concentric holes 102 in the inner cylinder 106 and outer spherical feature 107 will rotate the two axes out of alignment and create the interference, via articulating surface 100, and the engagement of the inner cylinder 106 with the post 16, caused by the outer spherical feature 107.

In one embodiment, fixation system 10 may be treated with or include an agent, which may be disposed, packed or layered within, on or about the components and/or surfaces of system 10. It is envisioned that the agent may include bone growth promoting material, such as, for example, bone graft to enhance fixation of the fixation device 10 with spinal processes of vertebrae.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of fixation system 10 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal fixation system, comprising:
    a first plate configured to be positioned to span between spinal processes of two adjacent vertebrae;
    a post having one end fixedly attached to the first plate and a distal second end;
    a second plate positioned opposite said first plate and configured to receive the distal end of said post, said second plate being capable of at least axial translation along said post,
    a locking mechanism configured to restrict translation of the second plate along the post, the locking mechanism comprising: a tapered collet disposed around the post; and a tapered inboard surface of the second plate, wherein applying force to the tapered collet causes an interference fit between the second plate and the post and restricts axial translation of the second plate along said post.

2. The spinal fixation system as recited in claim 1, wherein said first plate and said second plate comprise at least one spike configured to engage a spinal process.

3. The spinal fixation system as recited in claim 1, wherein said post is centrally attached to said first plate, and centrally received by said second plate.

4. The spinal fixation system as recited in claim 1, further comprising means for enabling orbital rotation of said second plate with respect to said post.

5. The spinal fixation system according to claim 1, wherein said first plate further comprises a plurality of spinal process engaging spikes on an inboard surface thereof, and said second plate further comprises a plurality of spinal process engaging spines on an inboard surface thereof.

6. A spinal fixation system, comprising:
    a first plate configured to be positioned on one side of two spinal processes of two adjacent vertebrae;
    a post having one end fixedly attached to the first plate and a distal second end;
    a second plate positioned on an opposite side of the two spinal processes and being configured to receive the distal end of said post, said second plate being capable of at least axial translation along said post; and
    a locking mechanism cooperative with said post and said second plate to lock and restrict at least one of axial translation and orbital rotation of said second plate with respect to said post, wherein said locking mechanism comprises: a tapered collet disposed around the post; and a tapered inboard surface of the second plate, wherein applying force to the tapered collet causes an interference fit between the second plate and the post and restricts axial translation of the second plate along said post.

7. The spinal fixation system as recited in claim 6, wherein said locking mechanism comprises:
    a tapered collet disposed around the post;
    a spherical collar disposed around the tapered collet and having an inner tapered surface and an outer spherical surface;
    an inboard spherical surface of the second plate configured to cooperate with the outer spherical surface of the spherical collar to provide orbital motion of the second plate with respect to the post;
    wherein applying force to the tapered collet causes an interference fit between the tapered collet and the inner tapered surface of the spherical collar and operates to restrict both axial translation and orbital rotation of the second plate.

8. The spinal fixation system as recited in claim 7, wherein said locking mechanism further comprises a snap feature integrated into said tapered collet and the inner tapered surface of the spherical collar, said snap feature further securing the locked position of the second plate onto the post.

9. The spinal fixation system as recited in claim 7, wherein said locking mechanism further comprises:
    a locking nut comprising:
        an inner cylinder having a central bore having central axis, and
        an outer cylinder having a central bore having a central axis, wherein said central bore of said inner cylinder is non-concentric with the central bore of said outer cylinder;
    wherein the central axes of the inner cylinder and outer cylinder can be aligned so as to receive the post, and wherein rotation of the outer cylinder causes the central axes of the inner and outer cylinders to un-align and results in an interference fit between the locking nut and the post.

10. The spinal fixation system as recited in claim 9, wherein said locking nut further comprises a break off feature configured to control applied torque to lock the second plate to the post.

11. The spinal fixation system as recited in claim 6, wherein said locking mechanism further comprises a snap feature integrated into said tapered collet and the inboard tapered surface of the second plate, said snap feature further securing the locked position of the second plate onto the post.

12. The spinal fixation system as recited in claim 6, wherein said locking mechanism further comprises:
    a locking nut comprising:
        an inner cylinder having a central bore having central axis, and
        an outer cylinder having a central bore having a central axis, wherein said central bore of said inner cylinder is non-concentric with the central bore of said outer cylinder;
    wherein the central axes of the inner cylinder and outer cylinder can be aligned so as to receive the post, and wherein rotation of the outer cylinder causes the central axes of the inner and outer cylinders to un-align and results in an interference fit between the locking nut and the post.

13. The spinal fixation system as recited in claim 12, wherein said locking nut further comprises a break off feature configured to control applied torque to lock the second plate to the post.

14. The spinal fixation system as recited in claim 12, wherein said locking mechanism further comprises:
    an articulating surface on an outboard surface of said second plate; and
    a corresponding articulating surface on a tip of the outer cylinder.

15. The spinal fixation system as recited in claim 12, wherein said inner cylinder is integrated into said second plate.

16. The spinal fixation system as recited in claim 12, wherein said inner cylinder comprises an outer thread, and said outer cylinder comprises an inner thread configured to engage the outer thread of the inner cylinder.

17. A spinal fixation system comprising:
    a first plate configured to be positioned on one side of two spinal processes of two adjacent vertebrae, said first plate having a plurality of spikes for securing the first plate in position against the two spinal processes;
    a cylindrical cross-section post having one end fixedly attached to the first plate and a distal second end;
    a second plate positioned on an opposite said of the two spinal processes and being configured to receive the distal end of said post, said second plate being capable of at least axial translation along said post and having a plurality of spikes for securing the second plate in position against the two spinal processes;
    a locking nut configured to restrict translation of the second plate along the post, the locking nut comprising:
        an inner cylinder having a central bore having central axis, and
        an outer cylinder having a central bore having a central axis, wherein said central bore of said inner cylinder is non-concentric with the central bore of said outer cylinder, said outer cylinder having a proximal nut for rotating the outer cylinder and a removal nut for enabling removal of the locking nut from the post; and
    a break off feature configured to control applied torque to lock the second plate to the post;
    wherein the central axes of the inner cylinder and outer cylinder are initially aligned to receive the post, and wherein rotation of the outer cylinder causes the central axes of the inner and outer cylinders to un-align and results in an interference fit between the locking nut and the post.

18. The spinal fixation system as recited in claim 17, further comprising:
    an orbital rotation locking system cooperative with said second plate and said post to restrict orbital rotation of said second plate with respect to said post.

19. A method for correction of a spine disorder, the method comprising the steps of:
    providing access to a surgical site at a selected section of a spine;
    providing a spinal fixation system including
        a first plate configured to be positioned on one side of two spinal processes of two adjacent vertebrae;
        a post having one end fixedly attached to the first plate and a distal second end;
        a second plate positioned on an opposite side of the two spinal processes and being configured to receive the distal end of said post, said second plate being capable of at least axial translation along said post; and
        a locking mechanism cooperative with said post and said second plate to lock and restrict at least one of axial translation and orbital rotation of said second plate with respect to said post;
    positioning the first plate against the two spinal processes;
    positioning the second plate onto the post;
    adjusting an axial position of the second plate along the post;
    adjusting an orbital rotation position of the second plate with respect to said post; and
    locking the axial translation and orbital rotation position using the locking mechanism.

* * * * *